United States Patent [19]
Ida et al.

[11] Patent Number: 5,789,572
[45] Date of Patent: Aug. 4, 1998

[54] METHOD FOR THE PREPARATION OF 1,4,-ANHYDRO-2-DEOXY-D-ERYTHROPENTITOL

[75] Inventors: Yutaka Ida; Satoshi Kikuchi; Shinobu Iriuchijima. all of Gunma-ken. Japan

[73] Assignee: Nikko Rica Co., Ltd., Japan

[21] Appl. No.: 864,962

[22] Filed: May 29, 1997

[30] Foreign Application Priority Data

May 31, 1996 [JP] Japan .................................. 8-137822

[51] Int. Cl.$^6$ .............................. C07H 1/00; C07H 15/02
[52] U.S. Cl. ............................................. 536/124; 536/1.11
[58] Field of Search ............................................. 536/124

[56] References Cited

FOREIGN PATENT DOCUMENTS 289591  12/1987  Japan .

OTHER PUBLICATIONS

Chemical Abstracts No. 107:227936m, JP Kokai 62 289591, 1987.
Lin et al., *Chemical Abstracts*, vol. 122:213847(f) (1995).
A. Holy "Preparation of Enantiomeric and Racemic 2,3,4–5–Tetrahydroxypentyl Derivatives of Adenine, Cytosine and Uracil", Collection Czechoslovak Chem. Commun., vol. 47, pp. 2786–2805, 1982.
A. Tymiak et al. "Structures of Kelletinins I and II, Antibacterial Metabolites of the Marine Mollusk *Kelletia kelletii*", J. Am. Chem. Soc., vol. 105, pp. 7396–7401, 1983.
J. Plavec et al., "How do the Gauche and Anomeric Effects Drive the Pseudorotational Equilibrium of the Pentofuranose Moiety of Nucleosides?", J. Am. Chem. Soc., vol. 115, pp. 9734–9746, 1993.

*Primary Examiner*—Gary L. Kunz
*Attorney, Agent, or Firm*—Wenderoth, Lind & Ponack, L.L.P.

[57] ABSTRACT

Proposed is a novel synthetic route for the preparation of 1,4-anhydro-2-deoxy-D-erythropentitol, which is a useful material in the synthesis of antibiotics, starting from 2-deoxy-D-ribose via 2-deoxy-D-erythropentitol as an intermediate. 2-Deoxy-D-erythropentitol can be prepared by the hydrogenation of 2-deoxy-D-ribose with Raney nickel as the hydrogenating catalyst in a high efficiency and at low costs as compared with the prior art methods using, for example, sodium borohydride as the hydrogenating agent. 2-Deoxy-D-erythropentitol is subjected to a dehydration cyclization reaction to be converted into 1,4-anhydro-2-deoxy-D-erythropenti-tol under a substantially anhydrous condition which is accomplished by heating a reaction mixture containing 2-deoxy-D-erythropentitol suspended in an organic solvent capable of forming an azeotropic mixture with water such as toluene under reflux so as to azeotropically remove the water condensate.

9 Claims, No Drawings

METHOD FOR THE PREPARATION OF 1,4,-ANHYDRO-2-DEOXY-D-ERYTHROPENTITOL

BACKGROUND OF THE INVENTION

The present invention relates to a method for the preparation of 1,4-anhydro-2-deoxy-D-erythropentitol or, more particularly, to a synthetic method for the preparation of 1,4-anhydro-2-deoxy-D-erythropentitol from 2-deoxy-D-ribose as the starting material via 2-deoxy-D-erythropentitol as an intermediate.

It is well known that 1,4-anhydro-2-deoxy-D-erythropentitol is a compound having usefulness as a base material for the synthesis of certain antibiotics (see, for example, Japanese Patent Kokai 6-321948. It is also known that 1,4-anhydro-2-deoxy-D-erythropentitol can be obtained, according to the teaching in the above mentioned Japanese patent document, by the dehydration cyclization reaction, in hydrochloric acid, of 2-deoxy-D-erythropentitol as an intermediate which in turn is obtained by the reduction of 2-deoxy-D-ribose by the use of sodium borohydride as a reducing agent according to the disclosure in, for example, Coll. Czech. Chem. Commun., volume 47, page 2786 (1982), J. Am. Chem. Soc., volume 105, page 7401 (1983) and Japanese Patent Kokai 62-289591. Alternatively, J. Am. Chem. Soc., volume 115, page 9734 (1993) teaches a method for the preparation of 1,4-anhydro-2-deoxy-D-erythropentitol in five steps including (1) methoxylation of 2-deoxy-D-ribose with hydrogen chloride and methyl alcohol, (2) di-acylation of the reaction product in step (1), (3) chlorination of the reaction product in step (2) with hydrogen chloride and acetic acid, (4) reductive dechlorination of the reaction product in step (3) with tributyltin hydride and (5) deacylation of the reaction product in step (4).

The above described synthetic routes for the preparation of 1,4-anhydro-2-deoxy-D-erythropentitol are each not practicable as an industrial method due to one or more serious problems and disadvantages. For example, the reducing reaction of 2-deoxy-D-ribose for the preparation of 2-deoxy-D-erythropentitol is disadvantageous because sodium borohydride as a very expensive reducing agent must be used in an excess amount if not to mention the complicated post-treatment of the reaction product including decomposition of the excess amount of the reducing agent, decationation by the use of an ion exchange resin and removal of boric acid.

The five-step method for the preparation of 1,4-anhydro-2-deoxy-D-erythropentitol from 2-deoxy-D-ribose is also not industrial because, besides the complicacy of the process involving so many steps, of the use of tributyltin hydride which is an extremely expensive reagent usable only for laboratory purposes.

The above mentioned method of dehydration cyclization of 2-deoxy-D-erythropentitol by the reaction with hydrochloric acid is also not industrially practicable because the reaction must be performed by heating 2-deoxy-D-erythropentitol dissolved in hydrochloric acid for 72 hours and the yield of the desired product is low if not to mention that the above recited reference is silent on the purity and the stereostructure of the reaction product obtained by the method.

SUMMARY OF THE INVENTION

The present invention accordingly has an object to provide a a reliable and inexpensive synthetic route for the preparation of 1,4-anhydro-2-deoxy-D-erythropentitol from 2-deoxy-D-ribose as the starting material via 2-deoxy-D-erythropentitol as the intermediate, in which the desired product having the exact stereo-structure can be efficiently prepared in a high yield.

Thus the present invention in the first aspect provides a method for the preparation of 2-deoxy-D-erythropentitol which comprises the step of hydrogenating 2-deoxy-D-ribose in the presence of a Raney catalyst which is preferably Raney nickel.

The invention in the second aspect provides a method for the preparation of 1,4-anhydro-2-deoxy-D-erythropentitol which comprises the step of reacting 2-deoxy-D-erythropentitol with an acid to effect dehydration cyclization of the 2-deoxy-D-erythropentitol under a substantially anhydrous condition. In particular, the substantially anhydrous condition can be accomplished by conducting the reaction of the 2-deoxy-D-erythropentitol with the acid in the presence of an organic solvent capable of forming an azeotropic mixture with water but incapable of dissolving the 2-deoxy-D-erythropentitol with heating of the reaction mixture under reflux of the solvent so as to remove the water produced by the dehydration reaction by azeotropic distillation with the organic solvent.

DETAILED DESCRIPTION OF THE PREFERRED EMBODIMENTS

As is described above, the subject matter in the first aspect of the present invention is a synthetic method for the preparation of 2-deoxy-D-erythropentitol by the hydrogenation of 2-deoxy-D-ribose. Different from the prior art method, in which the hydrogenating agent is expensive sodium borohydride, the inventive method is characterized by the use of a Raney catalyst such as Raney nickel, Raney cobalt and the like as the hydrogenating agent. Though not particularly limitative, Raney nickel is preferred as the Raney catalyst in respects of the high activity for hydrogenation and low cost as compared with Raney cobalt catalysts.

In practicing the inventive method for the preparation of 2-deoxy-D-erythropentitol, 2-deoxy-D-ribose as the starting material is dissolved in a solvent which can be water or a lower alcohol such as methyl and ethyl alcohols, of which water is preferred because water is free from the problem of environmental pollution by the organic waste liquid and has a high dissolving power of the starting material if not to mention the advantage due to inexpensiveness. The concentration of 2-deoxy-D-ribose in the thus prepared aqueous solution is usually in the range from 100 to 1000 g/liter or, preferably, from 200 to 500 g/liter.

The amount of the Raney catalyst or, in particular, Raney nickel added to the aqueous solution of the starting material is in the range from 5 to 30% by weight or, preferably, from 10 to 20% by weight based on the amount of the 2-deoxy-D-ribose though dependent on various factors such as the reaction temperature, hydrogen pressure and others. The hydrogenation reaction proceeds at a temperature in the range from room temperature to 150° C. or the reaction is performed preferably at a temperature in the range from 50° to 100° C. The pressure of hydrogen gas in the hydrogenation reaction is in the range from normal pressure to 150 kg/cm$^2$G or, preferably, in the range from 20 to 50 kg/cm$^2$G. When the hydrogenation reaction is performed under the above mentioned conditions, the reaction is complete usually within 1 to 2 hours.

After completion of the reaction and cooling, the reaction mixture taken out of the pressurizable reaction vessel is freed from the solid of the Raney catalyst by filtration or other suitable means to give a filtrate which is an aqueous solution of the desired 2-deoxy-D-erythropentitol which can be isolated from the reaction mixture by evaporating the solvent. The yield of this reaction product is usually almost quantitative.

The subject matter in the second aspect of the present invention is a method for the preparation of 1,4-anhydro-2-deoxy-D-erythropentitol by the dehydrating cyclization of 2-deoxy-D-erythropentitol in the presence of a catalytic amount of an acid. The most characteristic feature of the invention is that this dehydration cyclization reaction is performed under a substantially anhydrous condition in contrast to the prior art method in which an aqueous solution of 2-deoxy-D-erythropentitol containing hydrochloric acid is heated under boiling.

The acid used as the catalyst of the reaction can be selected from the group consisting of arenesulfonic acids such as benzene-sulfonic acid, p-toluenesulfonic acid and the like, alkanesulfonic acids such as methanesulfonic acid, ethanesulfonic acid and the like, ion-exchange resins having sulfonic acid residue, inorganic acids such as sulfuric acid and the like and Lewis acids such as boron trifluoride and the like, of which arenesulfonic acids are preferred in respect of the relatively high yield of the desired product, i.e. 1,4-anhydro-2-deoxy-D-erythropentitol, obtained therewith. The amount of the acid catalyst is in the range, usually, from 0.1 to 10% by weight or, preferably, from 0.5 to 5% by weight based on the amount of the 2-deoxy-D-erythropentitol as the starting material of the reaction.

In practicing the dehydration cyclization reaction of 2-deoxy-D-erythropentitol, this starting material is suspended in an organic solvent, which is capable of forming an azeotropic mixture with water but incapable of dissolving the starting material, such as aromatic hydrocarbon solvents, e.g., benzene, toluene, chlorobenzene and the like, and aliphatic hydrocarbon solvents, e.g., cyclohexane, methylcyclohexane, octane and the like, which is a solvent capable of forming an azeotropic mixture with water, containing an acid catalyst mentioned above to form a reaction mixture. The solvent is preferably an aromatic hydrocarbon solvent or, more preferably, toluene in view of the safety problem and the yield of the reaction product. The amount of the solvent in the reaction mixture is usually in the range from 0.3 to 10 times by weight or, preferably, from 0.5 to 5 times by weight based on the amount of 2-deoxy-D-erythropentitol.

The reaction is performed by heating the reaction mixture under reflux of the solvent. Namely, the reaction temperature, which usually depends on the kind of the solvent used, is usually in the range from 80° to 200° C. or, in most cases, from 100° to 180° C. It is convenient that the reflux condenser on the reaction vessel is provided with a suitable water-separating adaptor such as the Dean-Stark's separator by means of which the condensate of water produced by the dehydration reaction and distilled out of the reaction mixture as an azeotropic mixture with the organic solvent can be discarded out of the reaction system with the organic solvent alone returned back to the reaction mixture so as to facilitate to ensure the desired substantially anhydrous condition of the reaction mixture.

When the dehydration cyclization reaction of 2-deoxy-D-erythropentitol is performed under the above described conditions, the reaction is complete usually within 4 to 5 hours. After completion of the reaction and cooling, the reaction mixture is admixed with an appropriate amount of an alkaline compound such as sodium hydrogencarbonate to neutralize the acid catalyst followed by filtration to remove the solid material. The filtrate is then subjected to stripping distillation to remove the solvent and the thus obtained crude product is distilled to isolate 1,4-anhydro-2-deoxy-D-erythropentitol in a high purity as an oily liquid. The yield of the product is usually at least 80% based on the amount of the 2-deoxy-D-erythropentitol.

Since the thus obtained product is an oily liquid, identification of the product can be performed by converting the compound into the dimethanesulfonate of the compound having a definite melting point, to which various analytical identification methods can be applied, according to a procedure known in the art.

In the following, the method of the invention is illustrated in more detail by way of examples.

EXAMPLE 1

An 80 g (0.60 mole) portion of 2-deoxy-D-ribose was dissolved in 240 ml of water to form an aqueous solution into which 15 g of Raney nickel were added. The thus prepared reaction mixture in an autoclave was heated under a hydrogen pressure of 40 kg/cm$^2$G up to a temperature of 70° C. taking 30 minutes and kept for additional 1 hour at the same temperature and under the same hydrogen pressure. After cooling, the reaction mixture taken out of the autoclave was filtered to remove the solid catalyst and the filtrate, as combined with the washings of the solid catalyst with water, was subjected to removal of the water to give about 80 g of 2-deoxy-D-erythropentitol. The yield of the product was almost quantitative.

EXAMPLE 2

A 100 g (0.75 mole) portion of 2-deoxy-D-ribose was dissolved in 200 ml of water to form an aqueous solution into which 20 g of Raney nickel were added. The thus prepared reaction mixture in an autoclave was heated under a hydrogen pressure of 40 kg/cm$^2$G up to a temperature of 70° C. taking 30 minutes and kept for additional 1 hour at the same temperature and under the same hydrogen pressure. After cooling, the reaction mixture taken out of the autoclave was filtered to remove the solid catalyst and the filtrate, as combined with the washings of the solid catalyst with water, was subjected to removal of the water to give about 100 g of 2-deoxy-D-erythropentitol. The yield of the product was almost quantitative.

EXAMPLE 3

A reaction mixture prepared by adding 80 g of the 2-deoxy-D-erythropentitol obtained in the preceding Examples and 2.2 g (0.012 mole) of p-toluenesulfonic acid monohydrate in 50 ml of toluene was heated under reflux in a reaction vessel equipped with a water distillate separating adaptor with periodical discarding of the water produced by the dehydration and distilled out as an azeo-tropic mixture with toluene to be separated in the adaptor. The reaction was continued in this manner for about 4 hours until distillation-out of the condensation water ceased indicating completion of the reaction.

After cooling, the reaction mixture was admixed with 1.3 g (0.015 mole) of sodium hydrogencarbonate to neutralize the acid catalyst followed by removal of the solid material by filtration. The filtrate was stripped of toluene and then subjected to distillation under reduced pressure to give 56.1 g of an oily material as the reaction product as a fraction boiling at 104° to 106° C. under a pressure of 1 Torr. The liquid product having a gas chromatographic purity of 97.6% could be identified to be 1,4-anhydro-2-deoxy-D-erythropentitol from the results of the identification tests shown below. The above mentioned yield of the product corresponds to 80% of the theoretical value based on 2-deoxy-D-ribose.

Identification of the above obtained reaction product was performed in the following manner. Thus, 9.5 g of the product were dissolved in a mixture of 100 ml of dichloromethane and 24.5 g (0.24 mole) of triethylamine to form a solution, which was, under chilling in an ice water bath with agitation, admixed with a solution of 23.1 g (0.20 mole) of methanesulfonyl chloride in 20 ml of dichloromethane dropwise over a period of 10 minutes. Agitation of the mixture was continued for further 2 hours at room temperature with the ice water bath removed. Thereafter, the mixture was admixed with water and acidified with a small amount of sulfuric acid followed by extraction with dichloromethane to give an organic extract solution which was dehydrated and freed from the solvent to leave a concentrate.

The concentrate was dissolved in 400 ml of hot methyl alcohol and the solution after cooling with water was admixed with several seed crystals of 1,4-anhydro-2-deoxy-D-erythropentitol di-methanesulfonate under agitation so that crystals could be obtained as precipitates in the mixture in an amount of 5.7 g as dried. This crystalline product could be identified to be 1,4-anhydro-2-deoxy-D-erythropentitol dimethanesulfonate from the analytical results shown below.

The mother liquor after separation of the crystalline precipitates was concentrated into a half volume by evaporating a part of the solvent and the concentrated mother liquor was again cooled with water and subjected to second crystallization-out of the crystalline precipitates in an amount of 3.7 g as dried. The mother liquor after separation of the second crystallization product was further concentrated and subjected to the silica gel chromatography with dichloromethane as the eluant solvent to give 7.4 g of the product compound. The overall yield of the product as a total of the three fractions was 77% as a sum of 26%, 17% and 34% for the first, second and third steps of the preparation, respectively.

Analytical data Melting point: 47° to 49° C. Specific rotation[a]$D^{20}$: +40.30 (c=1, acetone) 60 Hz NMR (CDCl$_3$, ppm):

1.9 to 2.5 (2H); 3.1 (6H, s); 3.8 to 4.4 (5H); 5.1 (1H, m)

| Elementary analysis: | | |
| --- | --- | --- |
|  | C | H |
| calculated for $C_7H_{14}O_7S_2$ | 30.65% | 5.14% |
| found | 30.86% | 5.13% |

What is claimed is:

1. A method for the preparation of 1,4-anhydro-2-deoxy-D-erythropentitol which comprises the step of subjecting 2-deoxy-D-erythropentitol to a dehydration cyclization reaction in the presence of an acid under a substantially anhydrous condition.

2. The method for the preparation of 1,4-anhydro-2-deoxy-D-erythropentitol as claimed in claim 1 in which the acid is selected from the group consisting of arenesulfonic acids, alkanesulfonic acids, ion exchange resins having sulfonic acid groups, sulfuric acid and Lewis acids.

3. The method for the preparation of 1,4-anhydro-2-deoxy-D-erythropentitol as claimed in claim 2 in which the acid is an arene-sulfonic acid.

4. The method for the preparation of 1,4-anhydro-2-deoxy-D-erythropentitol as claimed in claim 3 in which the arenesulfonic acid is p-toluenesulfonic acid.

5. The method for the preparation of 1,4-anhydro-2-deoxy-D-erythropentitol as claimed in claim 1 in which the amount of the acid is in the range from 0.1% to 10% by weight based on the amount of the 2-deoxy-D-erythropentitol.

6. The method for the preparation of 1,4-anhydro-2-deoxy-D-erythropentitol as claimed in claim 1 in which the substantially anhydrous condition of the dehydration cyclization reaction is accomplished by heating a reaction mixture containing the 2-deoxy-D-erythropentitol suspended in an organic solvent capable of forming an azeotropic mixture with water under reflux and discarding water as a condensate of the azeotropic distillate out of the reaction mixture.

7. The method for the preparation of 1,4-anhydro-2-deoxy-D-erythropentitol as claimed in claim 6 in which the organic solvent capable of forming an azeotropic mixture with water is an aroma- tic hydrocarbon solvent.

8. The method for the preparation of 1,4-anhydro-2-deoxy-D-erythropentitol as claimed in claim 7 in which the aromatic hydrocarbon solvent is toluene.

9. The method for the preparation of 1,4-anhydro-2-deoxy-D-erythropentitol as claimed in claim 6 in which heating of the reaction mixture is performed at a temperature in the range from 80° C. to 200° C.

* * * * *